United States Patent
Mou et al.

(10) Patent No.: US 10,952,623 B2
(45) Date of Patent: Mar. 23, 2021

(54) WEARABLE BLOOD PRESSURE MEASURING DEVICE

(71) Applicant: Microjet Technology Co., Ltd., Hsinchu (TW)

(72) Inventors: Hao-Jan Mou, Hsinchu (TW); Shih-Chang Chen, Hsinchu (TW); Jia-Yu Liao, Hsinchu (TW); Yung-Lung Han, Hsinchu (TW); Chi-Feng Huang, Hsinchu (TW); Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 315 days.

(21) Appl. No.: 16/163,946

(22) Filed: Oct. 18, 2018

(65) Prior Publication Data
US 2019/0133454 A1   May 9, 2019

(30) Foreign Application Priority Data
Nov. 7, 2017   (TW) ................. 106138512

(51) Int. Cl.
*A61B 5/021* (2006.01)
*A61B 5/022* (2006.01)
(Continued)

(52) U.S. Cl.
CPC .......... *A61B 5/022* (2013.01); *A61B 5/02141* (2013.01); *A61B 5/681* (2013.01);
(Continued)

(58) Field of Classification Search
CPC ..... A61B 5/00; A61B 5/0022; A61B 5/02224; A61B 5/02; A61B 2562/14;
(Continued)

(56) References Cited

U.S. PATENT DOCUMENTS

2010/0121206 A1*  5/2010  Bae ................. A61B 5/02233
                                                          600/493
2016/0034696 A1   2/2016  Jooste et al.
(Continued)

FOREIGN PATENT DOCUMENTS

CN      103002797 A      3/2013
CN      106974632 A  *   7/2017  ........ A61B 5/0225
(Continued)

OTHER PUBLICATIONS

Extended European Search Report dated Mar. 18, 2019, for European Application No. 18201155.1.

*Primary Examiner* — Etsub D Berhanu
*Assistant Examiner* — Tyra Faith Bookhart
(74) *Attorney, Agent, or Firm* — Birch, Stewart, Kolasch & Birch, LLP (57) ABSTRACT

A wearable blood pressure measuring device includes a wristband, a valve plate, a gas-collecting seat, a gas transportation device, an elastic medium and a pressure sensor. The wristband has a mounting zone. The mounting zone has a first accommodation recess, a second accommodation recess, a gas-collecting hole and a pressure-releasing hole. The first accommodation recess and the second accommodation recess are in fluid communication with each other through the gas-collecting hole. When the gas transportation device is enabled to transport the gas to the elastic medium, the elastic medium is inflated with the gas and expanded to push the pressure sensor to be in close contact with a measurement part of a user's body, thereby measuring a blood pressure value of a target artery through a scanning operation.

13 Claims, 10 Drawing Sheets

(51) Int. Cl.
 *A61B 5/00* (2006.01)
 *A61B 5/024* (2006.01)
(52) U.S. Cl.
 CPC ........ *A61B 5/6824* (2013.01); *A61B 5/02438* (2013.01); *A61B 5/6831* (2013.01); *A61B 2562/0247* (2013.01)
(58) Field of Classification Search
 CPC .............. A61B 5/02141; A61B 5/0295; A61B 5/02225; A61B 5/6824; A61B 5/02438; A61B 2562/0247; A61B 5/68; A61B 5/6844; A61B 5/03; A61B 5/04; A61B 5/026; A61B 5/681; A61B 5/683–6831; A61B 5/6843–6844
 See application file for complete search history.

(56) References Cited

U.S. PATENT DOCUMENTS

2017/0218942 A1   8/2017  Chen et al.
2017/0222125 A1*  8/2017  Chen ..................... F04B 45/047

FOREIGN PATENT DOCUMENTS

| | | | | |
|---|---|---|---|---|
| KR | 10-1485717 B1 | 1/2015 | | |
| TW | 201608220 A | 3/2016 | | |
| TW | 201701825 A | 1/2017 | | |
| WO | WO 2016/040256 A1 | 3/2016 | | |
| WO | WO-2016040256 A1 * | 3/2016 | ........... | A61B 5/0053 |

* cited by examiner

WEARABLE BLOOD PRESSURE MEASURING DEVICE

FIELD OF THE INVENTION

The present disclosure relates to a wearable device, and more particularly to a wearable blood pressure measuring device having a gas transportation device, an elastic medium and a pressure sensor combined together.

BACKGROUND OF THE INVENTION

Nowadays, the pace of life becomes fast and the personal pressure is growing. As the awareness of the pursuit of personal health is gradually evolving, people want to regularly monitor or examine their health condition. Conventionally, the human physiological health information is measured through a fixed sphygmomanometer or a large-scale detection instrument. The detection instrument usually includes a motor-driven gas pump, an air bag, a sensor, a gas-releasing valve, a battery, and so on. During the operation of the motor-driven gas pump, the motor-driven gas pump is readily suffered from frictional loss. After these components are assembled, the volume of the product is large and thus the product is not suitable for frequent use. If a small-sized motor-driven gas pump is used, the frictional loss is increased and more energy is consumed.

For facilitating the ordinary persons to regularly monitor their own health conditions and allowing the monitoring device to be easily carried, many wearable health monitoring devices are introduced into the market. Generally, the wearable health monitoring devices are used for measuring the health conditions according to the optical detection technologies. Since the precision of the optical detection is not high enough, the detected value is possibly erroneous so that reliable data cannot be obtained effectively. Since the users fail to acquire accurate data relative to their health condition, the users may misjudge their health condition.

Generally, for measuring the physiological information of a user, a specified part of the user's body (e.g., head, heart, wrist or ankle) is monitored by a measuring device. At the specified part, the pulse blood pressure and heartbeat in the human body are sensed the most easily. By sensing the specified part, the physiological health information can be rapidly and effectively realized. As mentioned above, the precision of the wearable health monitoring device operated according to the optical detection technology is not high and the measured data is usually not reliable. Moreover, the commercially-available sphygmomanometers or other measuring instruments with higher reliability have bulky volume and fail to meet the requirements of small size, light weightiness and easy portability.

Therefore, there is a need of providing a wearable blood pressure measuring device in order to address the above-mentioned issues. The wearable blood pressure measuring device is small-sized, miniaturized, portable, power-saving and high-precise.

SUMMARY OF THE INVENTION

An object of the present disclosure provides a wearable blood pressure measuring device. The wearable blood pressure measuring device includes a gas transportation device, an elastic medium and a pressure sensor combined together. By transporting gas to the elastic medium through the piezoelectric-actuated gas transportation device, the elastic medium is inflated with the gas and expanded to raise the pressure sensor. Then, the pressure sensor disposed relative to the elastic medium is utilized to measure the blood pressure information of the user wearing the device. Thus, it solves the problems of the measuring instrument used in the prior art, which has a large volume, difficult to thin, consumes much power and cannot achieve the purpose of being portable. At the same time, it further solves the problem of low precision caused by the health monitoring device in the prior art, which detects through the optical detection method.

In accordance with an aspect of the present disclosure, a wearable blood pressure measuring device is provided. The wearable blood pressure measuring device includes a wristband, a valve plate, a gas-collecting seat, a gas transportation device, an elastic medium and a pressure sensor. The wristband has a mounting zone. The mounting zone includes a first accommodation recess, a second accommodation recess, a gas-collecting hole and a pressure-releasing hole. The first accommodation recess and the second accommodation recess are in fluid communication with each other through the gas-collecting hole. The first accommodation recess is in fluid communication with an environment outside the wristband through the pressure-releasing hole. The valve plate is stacked on an inner surface of the first accommodation recess. The valve plate has a valve opening aligned with the gas-collecting hole. The gas-collecting seat is disposed within the first accommodation recess and stacked on the valve plate. The gas-collecting seat has plural perforations. The gas transportation device covers and seals the gas-collecting seat for introducing gas through the plural perforations of the gas-collecting seat into the wearable blood pressure measuring device. The gas is introduced to push the valve plate that causes the valve opening of the valve plate to be in fluid communication with the gas-collecting hole so that the gas is further guided into and collected in the second accommodation recess. The elastic medium covers and seals the second accommodation recess and is configured to be inflated with the gas. The pressure sensor is stacked on the elastic medium. When the gas transportation device is enabled to transport the gas to the elastic medium, the elastic medium is inflated with the gas and expanded so as to push the pressure sensor to be in close contact with a measurement part of a user's body, thereby measuring a blood pressure value of a target artery through a scanning operation by pressing against the measurement part of the user's body.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
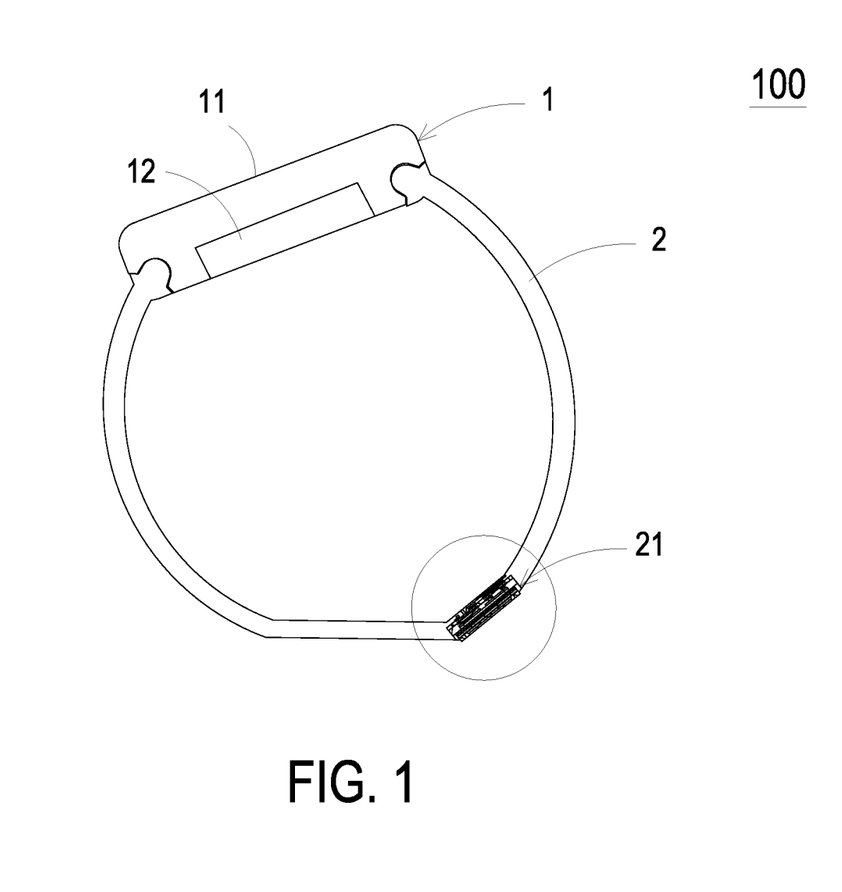
FIG. 1 schematically illustrates a wearable blood pressure measuring device according to an embodiment of the present disclosure.
Figure 2:
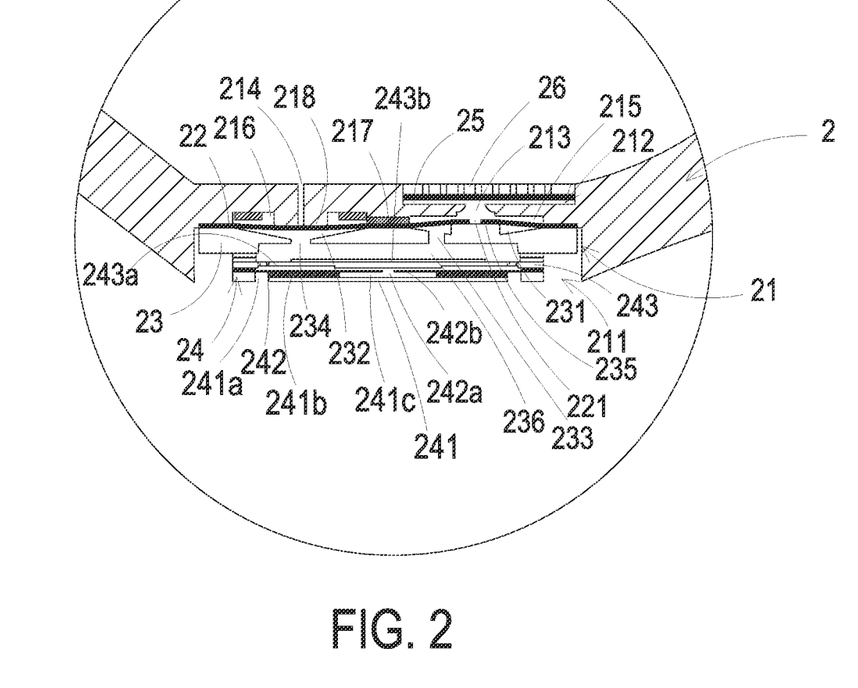
FIG. 2 is a schematic enlarged fragmentary view of the wearable blood pressure measuring device as shown in FIG. 1.

Please refer to FIGS. 1 and 2. The present discourse provides a wearable blood pressure measuring device 100 including at least one wristband 2, at least one mounting zone 21, at least one first accommodation recess 211, at least one second accommodation recess 212, at least one gas-collecting hole 213, at least one pressure-releasing hole 214, at least one valve plate 22, at least one valve opening 221, at least one gas-collecting seat 23, at least one gas transportation device 24, at least one elastic medium 25 and at least one pressure sensor 26. The number of the wristband 2, the mounting zone 21, the first accommodation recess 211, the second accommodation recess 212, the gas-collecting hole 213, the pressure-releasing hole 214, the valve plate 22, the valve opening 221, the gas-collecting seat 23, the gas transportation device 24, the elastic medium 25 and the pressure sensor 26 is exemplified by one for each in the following embodiments but not limited thereto. It is noted that each of the wristband 2, the mounting zone 21, the first accommodation recess 211, the second accommodation recess 212, the gas-collecting hole 213, the pressure-releasing hole 214, the valve plate 22, the valve opening 221, the gas-collecting seat 23, the gas transportation device 24, the elastic medium 25 and the pressure sensor 26 can also be provided in plural numbers.

Please refer to FIGS. 1 and 2. FIG. 1 schematically illustrates a wearable blood pressure measuring device according to an embodiment of the present disclosure. FIG. 2 is a schematic enlarged fragmentary view of the wearable blood pressure measuring device as shown in FIG. 1. The wearable blood pressure measuring device 100 may be worn on a wrist of the user, but not limited thereto. In this embodiment, the wearable blood pressure measuring device 100 includes a driving-and-control module 1 and a wristband 2. The wristband 2 of the wearable blood pressure measuring device 100 may be ring-shaped strap structure made of a soft material or a hard material. For example, the wristband 2 is made of a silicone material, a plastic material, a metallic material or any other appropriate material, but not limited thereto. The wristband 2 may be wrapped around a specified part of the user's body (e.g., the wrist or an ankle). The two ends of the wristband 2 are attached on each other through Velcro® fasteners, engaged with each other through convex-concave structures, or coupled with each other through the buckle rings often used in wristbands. Moreover, the wristband 2 may be a ring-shaped structure integrally formed from one piece. It is noted that the way of connecting the wristband 2 is not restricted and can be varied according to the practical requirements.

The wristband 2 of the wearable blood pressure measuring device 100 is not only wrapped around the specified part of the user's body but also used to carry the driving-and-control module 1 thereon. The connection between the wristband 2 and the driving-and-control module 1 may be undetachable or detachable. For example, the driving-and-control module 1 is integrated into the wristband 2, or the driving-and-control module 1 is locked on the wristband 2, but not limited thereto. The driving-and-control module 1 includes a processor (not shown) and a memory (not shown) for controlling the operation of the gas transportation device 24 and receiving the blood pressure information from the pressure sensor 26. In this embodiment, the driving-and-control module 1 further includes a display screen 11 disposed on the driving-and-control module 1 for displaying the blood pressure information, but not limited thereto. In an embodiment, the display screen 11 is a touch screen. The user may touch the screen display 11 to select the information to be displayed. The information contains at least one selected from the group consisting of the blood pressure information of the user, the time information, the incoming call information and so on.

In this embodiment, the wearable blood pressure measuring device 100 further includes a transmission module 12 disposed on the driving-and-control module 1. The transmission module 12 includes a wired transmission receiver (not shown) or a wireless transmission receiver (not shown) for transmitting the measured blood pressure information to an external device (not shown) via the wired transmission technique or the wireless transmission technique. The external device may analyze and process the measured blood pressure information to further learn the health condition of the user. It is noted that the position of the transmission module 12 is not restricted and can be varied according to the practical requirements. In some embodiments, the transmission module 12 is a wired transmission module. An example of the wired transmission module includes but is not limited to a USB transmission module, a mini-USB transmission module or a micro-USB transmission module. In some other embodiments, the transmission module 12 is a wireless transmission module. An example of the wireless transmission module includes but is not limited to a Wi-Fi transmission module, a Bluetooth transmission module, a radio frequency identification (RFID) transmission module or a near field communication (NFC) transmission module. In some other embodiments, the transmission module 12 may include a wired transmission module and a wireless transmission module. The type of the data to be transmitted may be varied according to practical requirements. Any implementation that transmits the physiological information (e.g., the blood pressure information) of the user stored in the driving-and-control module 1 to the external device is included in the claimed scope of the present disclosure, and not redundantly described hereinafter. In this embodiment, the external device may be for example but not limited to a cloud system, a portable electronic device or a computer system. After the external device receives the physiological information of the user from the wearable blood pressure measuring device 100, the health condition of the user may be clarified in more detail by running an application program that analyzes and compares the physiological information.

Please refer to FIG. 2 again. The wristband 2 has a mounting zone 21. The mounting zone 21 has a first accommodation recess 211, a second accommodation recess 212, a gas-collecting hole 213 and a pressure-releasing hole 214. The gas-collecting hole 213 is located between the first accommodation recess 211 and the second accommodation recess 212. The first accommodation recess 211 and the second accommodation recess 212 are in fluid communication with each other through the gas-collecting hole 213. The first accommodation recess 211 is in fluid communication with an environment outside the wristband 2 through the pressure-releasing hole 214. A first gas-collecting chamber 215 and a first pressure-releasing chamber 216 are concavely formed in the first accommodation recess 211 of the wristband 2. A communication channel 217 is located between the first gas-collecting chamber 215 and the first pressure-releasing chamber 216. Consequently, the first gas-collecting chamber 215 and the first pressure-releasing chamber 216 are in fluid communication with each other through the communication channel 217. The first gas-collecting chamber 215 is in fluid communication with the gas-collecting hole 213. The first pressure-releasing chamber 216 is in fluid communication with the pressure-releasing hole 214. A first convex structure 218 is received within the first pressure-releasing chamber 216 and is arranged around the pressure-releasing hole 214.

Please refer to FIGS. 2, 3A, 3B and 3C. The wearable blood pressure measuring device 100 further includes a valve plate 22, a gas-collecting seat 23, a gas transportation device 24, an elastic medium 25 and a pressure sensor 26. The valve plate 22 is stacked on an inner surface of the first accommodation recess 211. The valve plate 22 has a valve opening 221 aligned with the gas-collecting hole 213. The gas-collecting seat 23 is disposed within the first accommodation recess 211 and stacked on the valve plate 22. Moreover, the gas-collecting seat 23 has a second gas-collecting chamber 231, a second pressure-releasing chamber 232, plural perforations and a second convex structure 235. The plural perforations include a first perforation 233 and a second perforation 234. The first perforation 233 and the valve opening 221 (or the gas-collecting hole 213) are misaligned with each other. The second perforation 234 is aligned with the pressure-releasing hole 214 along the vertical direction. The gas transportation device 24 covers, seals and is stacked on the gas-collecting seat 23 for introducing the gas into the gas-collecting seat 23 and pushing the valve plate 22. Consequently, the valve opening 221 is in fluid communication with the gas-collecting hole 213. In such way, the gas is transported through the valve opening 221 and the gas-collecting hole 213 and guided into the second accommodation recess 212. Therefore, the gas is collected in the second accommodation recess 212.

Please refer to FIG. 2 again. The elastic medium 25 is disposed within the second accommodation recess 212 and in fluid communication with the gas-collecting hole 213. The fluid communication between the elastic medium 25 and the gas-collecting hole 213 allows the gas to flow into the elastic medium 25 through the gas-collecting hole 213. After the gas is introduced into the elastic medium 25 through the gas-collecting hole 213, the elastic medium 25 is inflated and expanded. The pressure sensor 26 is stacked on the elastic medium 25. After the elastic medium 25 is inflated and expanded, the pressure sensor 26 is pushed toward the wrist of the user to be in close contact with the user's skin. By pressing the pressure sensor 26 against the user's skin, the pressure sensor 26 can perform a scanning operation to measure a blood pressure value of a target artery of the user. In this embodiment, the pressure sensor 26 may be an array-type pressure sensor.

Please refer to FIG. 2. The gas-collecting seat 23 includes the second gas-collecting chamber 231, the second pressure-releasing chamber 232, the first perforation 233, the second perforation 234, the second convex structure 235 and a communication slot 236. The second gas-collecting chamber 231 is concavely formed in the gas-collecting seat 23 and corresponding in position with the first gas-collecting chamber 215. Consequently, the first gas-collecting chamber 215 and the second gas-collecting chamber 231 are collaboratively formed as an integrated gas-collecting chamber. The first gas-collecting chamber 215 and the second gas-collecting chamber 231 are separated from each other by the valve plate 22. When the valve opening 221 of the valve plate 22 moves away from the second convex structure 235, the valve opening 221 is in an open state. The open state allows the first gas-collecting chamber 215 and the second gas-collecting chamber 231 to be in fluid communication with each other through the valve opening 221. The second pressure-releasing chamber 232 is also concavely formed in the gas-collecting seat 23 and corresponding in position with the first pressure-releasing chamber 216. The first pressure-releasing chamber 216 and the second pressure-releasing chamber 232 are collaboratively formed as an integrated pressure-releasing chamber. The first pressure-releasing chamber 216 and the second pressure-releasing chamber 232 are separated from each other by the valve plate 22. The communication slot 236 is in fluid communication with the second gas-collecting chamber 231 through the first perforation 233. The first perforation 233 and the gas-collecting hole 213 are misaligned. The communication slot 236 is in fluid communication with the second pressure-releasing chamber 232 through the second perforation 234. The second perforation 234 and the pressure-releasing hole 214 are aligned with each other along the vertical direction. The second convex structure 235 is disposed adjacent to the first perforation 233. Moreover, the second convex structure 235 and the valve opening 221 of the valve plate 22 are aligned with each other along the vertical direction, but not limited thereto. Before the gas is introduced into the gas-collecting seat 23, the valve plate 22 is in close contact with the second convex structure 235. Under this circumstance, the valve opening 221 of the valve plate 22 is closed by the second convex structure 235.

When the gas is transported through the first perforation 233 and the second perforation 234 of the gas-collecting seat 23 to push the valve plate 22 to move, the valve opening 221 of the valve plate 22 is separated away from the second convex structure 235. Consequently, the valve opening 221 is in fluid communication with the gas-collecting hole 213, so that the gas is transported to the elastic medium 25 in the second accommodation recess 212 through the valve opening 221 and the gas-collecting hole 213. While the valve plate 22 is pushed by the gas introduced through the second perforation 234, the valve plate 22 is in close contact with the first convex structure 218 to close the pressure-releasing hole 214, so that the pressure-releasing hole 214 is sealed, which prevents the gas from leaking out of the pressure-releasing hole 214. In such way, the gas transported by the gas transportation device 24 is collected in and transported to the elastic medium 25.

Please refer to FIGS. 2, 3A, 3B and 3C. In this embodiment, the gas transportation device 24 includes a gas inlet plate 241, a resonance plate 242, a piezoelectric actuator 243, a first insulation plate 244, a conducting plate 245 and a second insulation plate 246, which are stacked on each other sequentially. The gas inlet plate 241 has at least one inlet aperture 241a, at least one convergence channel 241b and a convergence chamber 241c. The number of the at least one inlet aperture 241a and the number of the at least one convergence channel 241b are equal. For example, the gas inlet plate 241 has four inlet apertures 241a and four convergence channels 241b. A first end of the inlet aperture 241a is in fluid communication with the environment outside the gas transportation device 24. A second end of the inlet aperture 241a is in fluid communication with a first end of the corresponding convergence channel 241b. A second end of the convergence channel 241b is in communication with the convergence chamber 241c. As the gas is introduced into the gas transportation device 24 through the at least one inlet aperture 241a, the gas is transported to flow along the at least one convergence channel 241b and converged to the convergence chamber 241c.

Figure 3A:
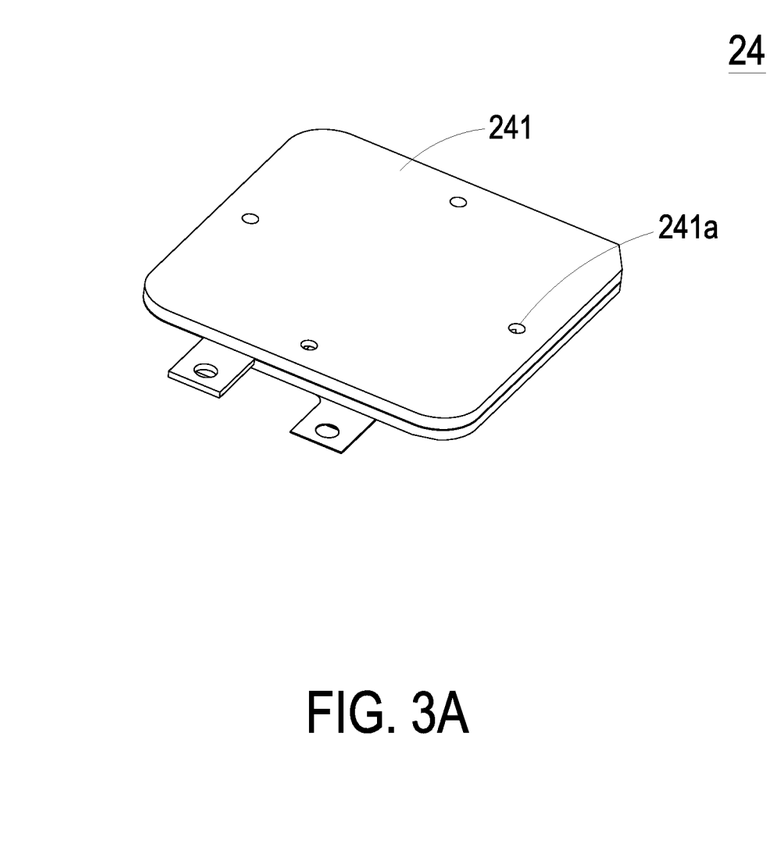
FIG. 3A is a schematic perspective view illustrating the gas transportation device of the wearable blood pressure measuring device according to the embodiment of the present disclosure and taken along the front side.
Figure 3B:
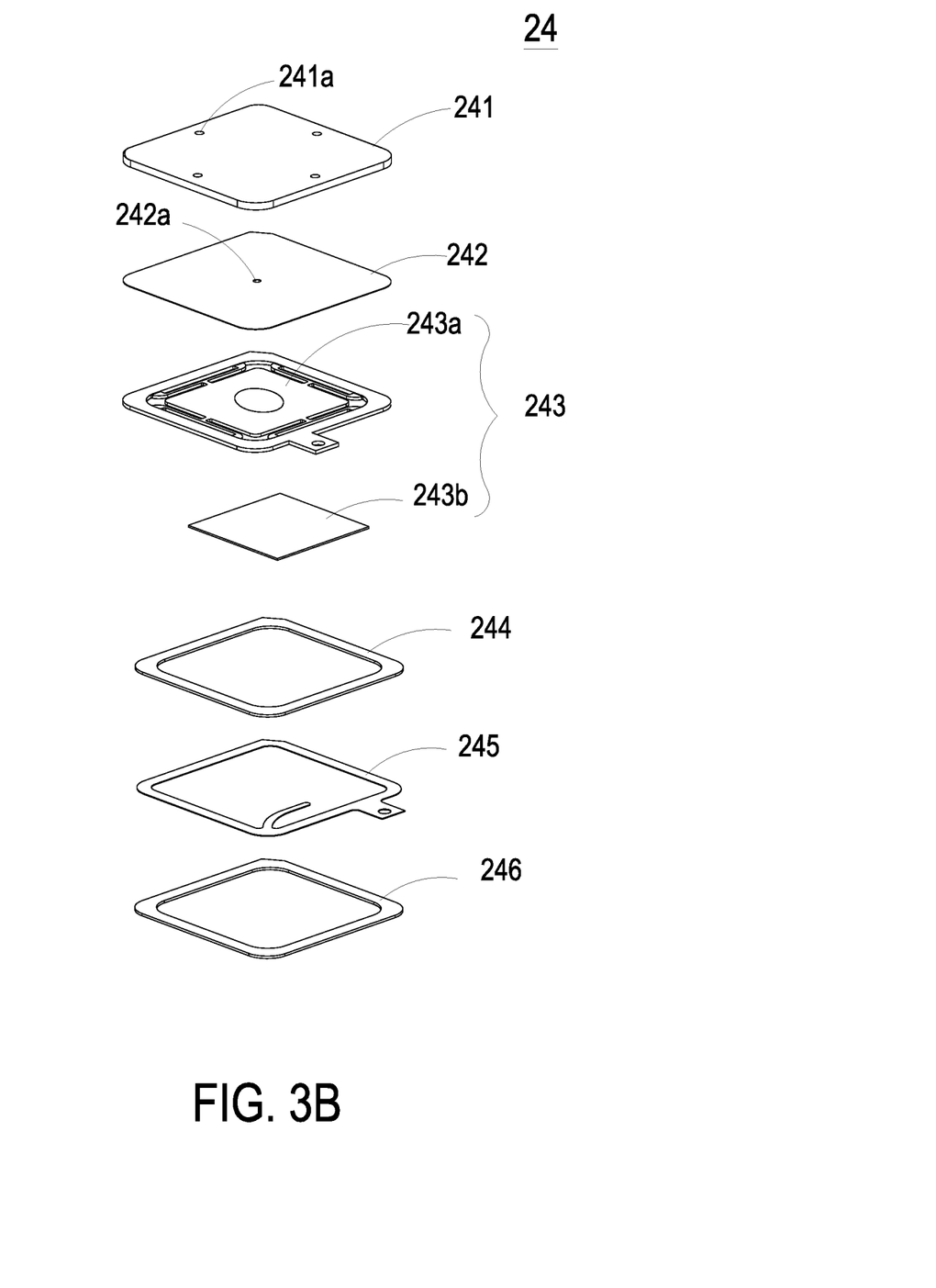
FIG. 3B is a schematic exploded view illustrating the gas transportation device as shown in FIG. 3A and taken along the front side.
Figure 3C:
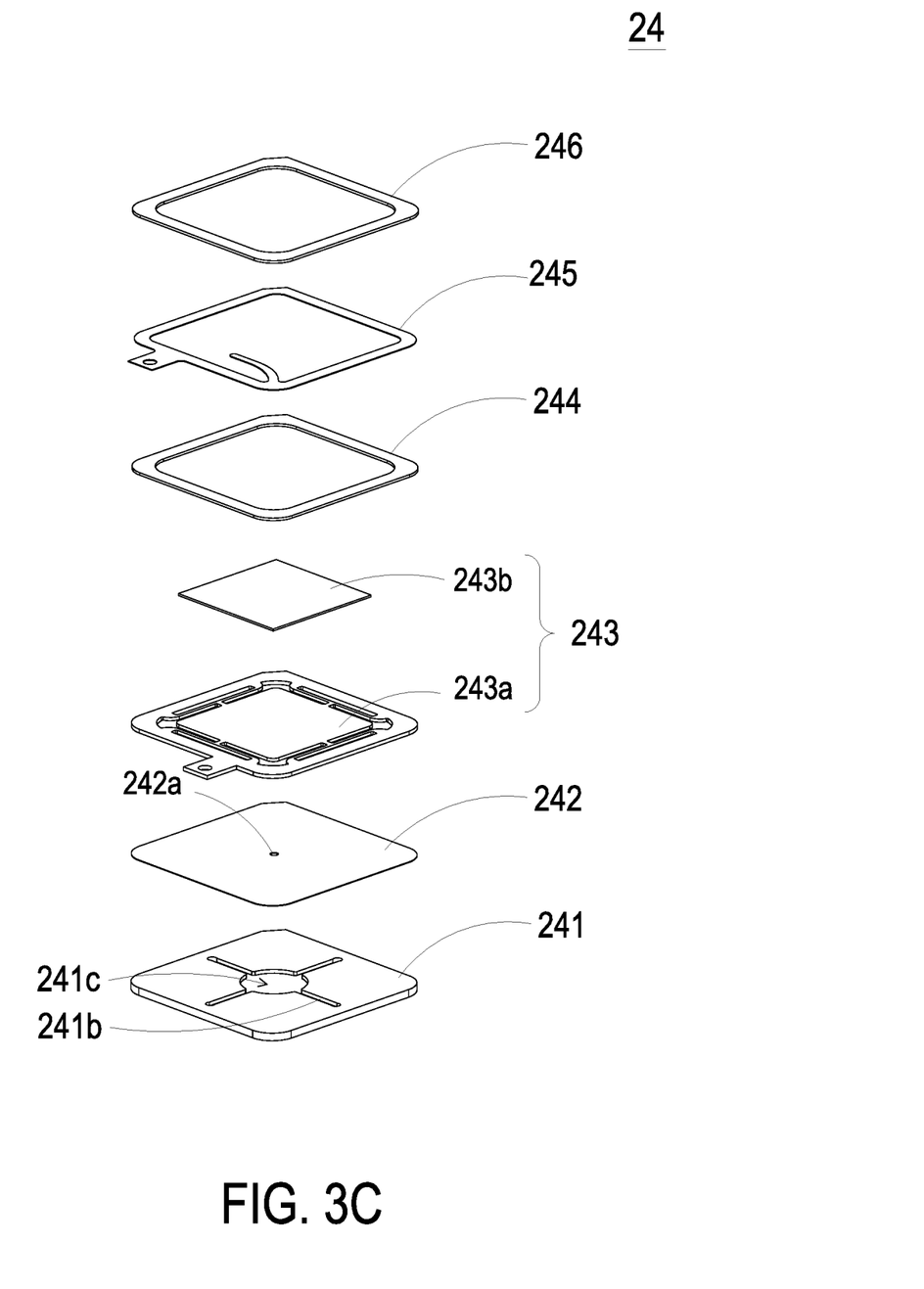
FIG. 3C is a schematic exploded view illustrating the gas transportation device as shown in FIG. 3A and taken along the rear side.

The resonance plate 242 has a central aperture 242a aligned with the convergence chamber 241c of the gas inlet plate 241 along the vertical direction. The resonance plate 242 has a movable part 242b around the central aperture 242a. The piezoelectric actuator 243 is corresponding in position with the resonance plate 242. The piezoelectric actuator 243 includes a suspension plate 243a and a piezoelectric plate 243b. The piezoelectric plate 243b is attached on a surface of the suspension plate 243a. Moreover, the profile of the piezoelectric plate 243b matches the profile of the suspension plate 243a. The length of a side of the piezoelectric plate 243b is smaller than or equal to the length of a side of the suspension plate 243a. When a voltage is applied to the piezoelectric plate 243b, the piezoelectric plate 243b is subjected to deformation according to a piezoelectric effect. Consequently, the suspension plate 243a vibrates upwardly and downwardly. At the same time, the resonance plate 242 vibrates in resonance with the suspension plate 243a.

Figure 4A:
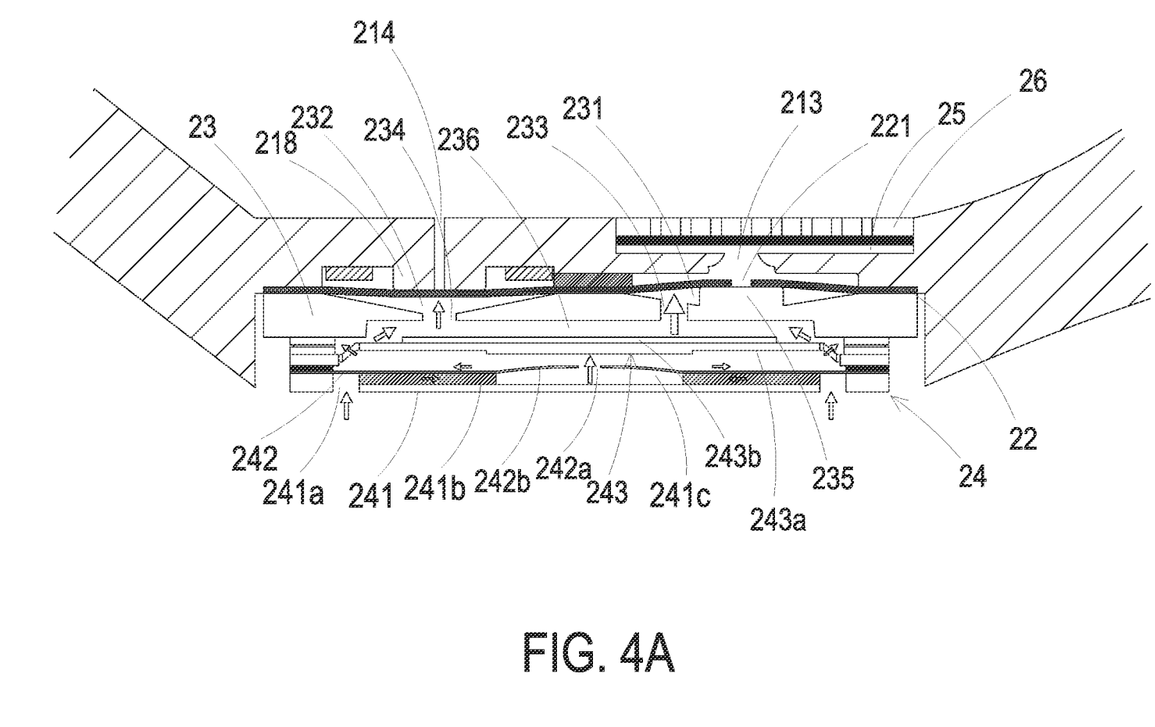
FIGS. 4A and 4B are schematic cross-sectional views illustrating the gas-collecting action of the gas transportation device of the wearable blood pressure measuring device according to the embodiment of the present disclosure.
Figure 4B:
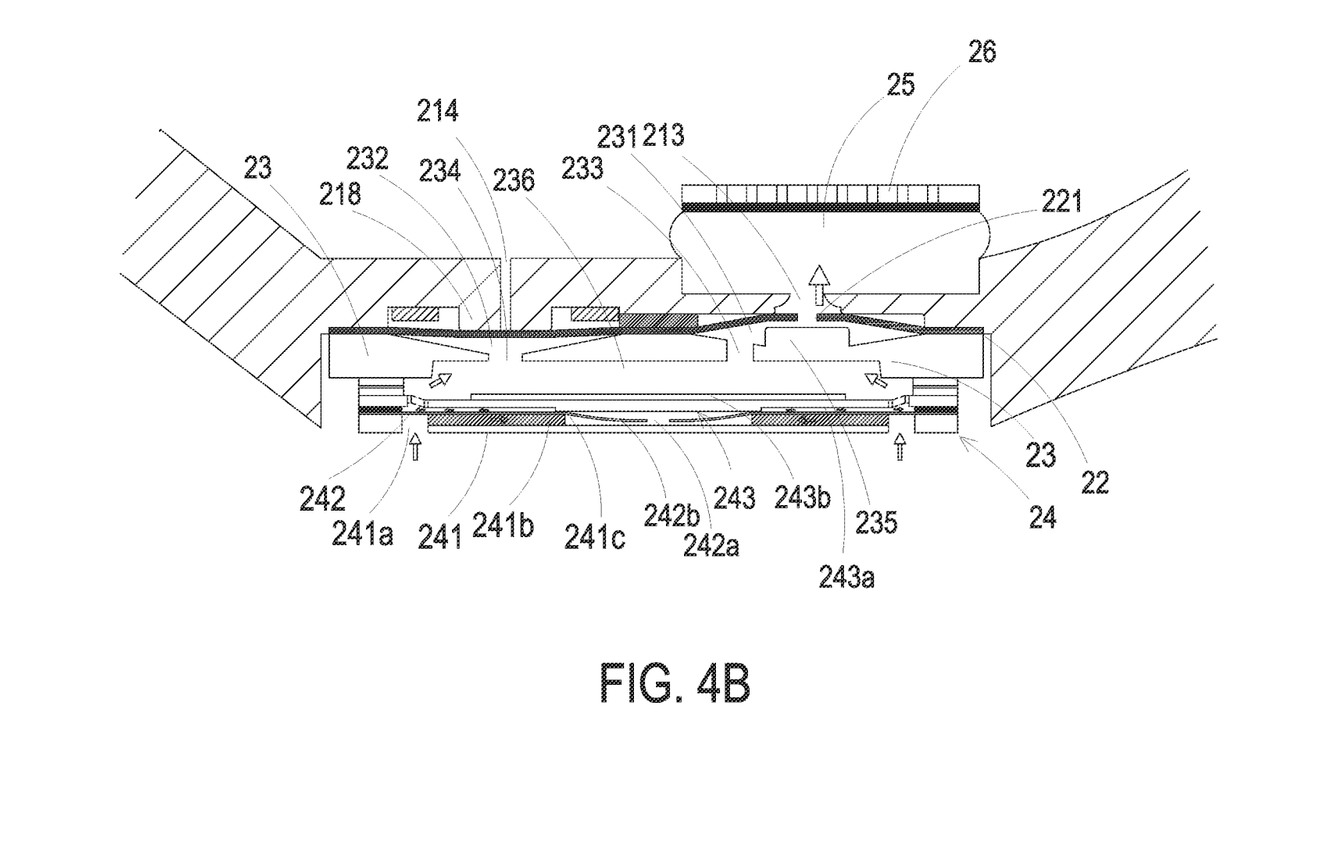

Please refer to FIGS. 4A and 4B. After the gas transportation device 24 is enabled, the piezoelectric plate 243b of the piezoelectric actuator 243 is driven by the applied voltage. Because of the piezoelectric effect, the piezoelectric plate 243b is subjected to the deformation and drives the suspension plate 243a to vibrate. After the piezoelectric actuator 243 is actuated, the movable part 242b of the resonance plate 242 vibrates in resonance with the suspension plate 243a. As the piezoelectric plate 243b drives the suspension plate 243a to move, the volume between the suspension plate 243a and the resonance plate 242 is changed. Consequently, the ambient gas is inhaled into the at least one convergence channel 241b through the at least one inlet aperture 241a, and the gas is guided by the at least one convergence channel 241b and converged to the convergence chamber 241c. Then, the gas is transported to an interior of the gas transportation device 24 through the central aperture 242a of the resonance plate 242. After the gas is transported to the communication slot 236, the gas is transported to the second gas-collecting chamber 231 and the second pressure-releasing chamber 232 through the first perforation 233 and the second perforation 234, respectively. Please refer to FIG. 4B. After the gas is introduced into the gas-collecting seat 23, the pressure of the gas pushes and moves the valve plate 22. The valve opening 221 of the valve plate 22 is separated from the second convex structure 235 and a pre-force that brings the valve opening 221 into close contact with the second convex structure 235 is eliminated. Consequently, the gas is transported to the gas-collecting hole 213 through the valve opening 221. At the same time, the valve plate 22 is in close contact with the first convex structure 218 to close the pressure-releasing hole 214. In this way, the gas is transported to the elastic medium 25 through the gas-collecting hole 213 and collected in the elastic medium 25. As the elastic medium 25 is inflated with the gas and expanded, the pressure sensor 26 is pushed by the expanded elastic medium 25. As the piezoelectric actuator 243 vibrates upwardly and downwardly, the gas continuously flows through the valve opening 221 and the gas-collecting hole 213 into the elastic medium 25 for collection of the gas. The elastic medium 25 is continuously expanded to lift the pressure sensor 26 up to a position that makes the pressure sensor 26 press against a measurement part of the user's body.

Figure 5:
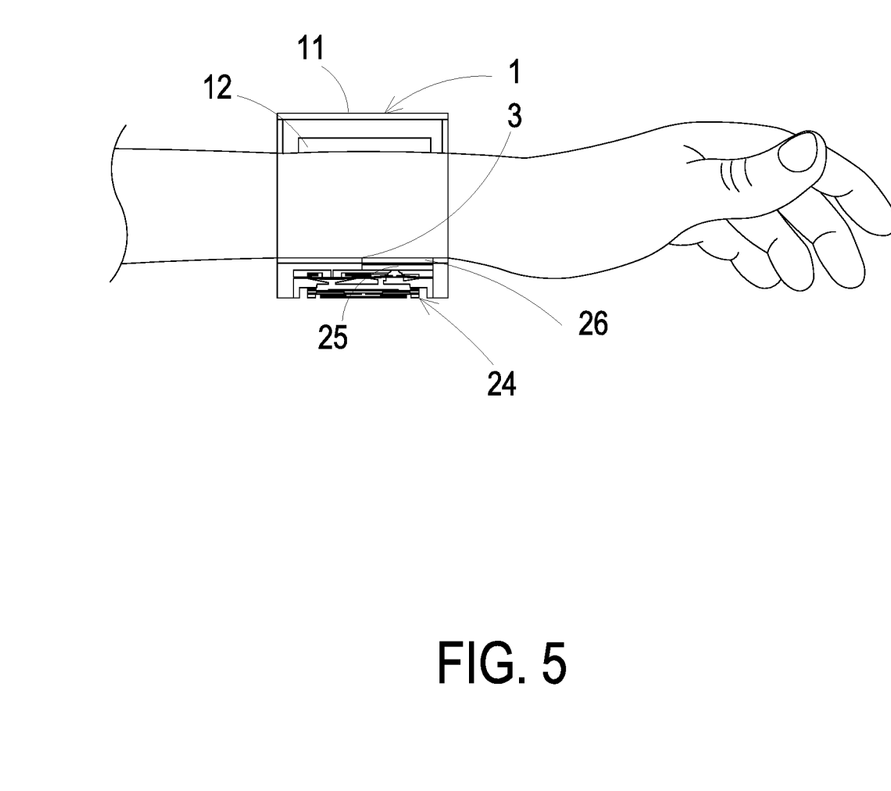
FIG. 5 schematically illustrates the scenario of wearing the wearable blood pressure measuring device on the wrist of the user.
Figure 6:
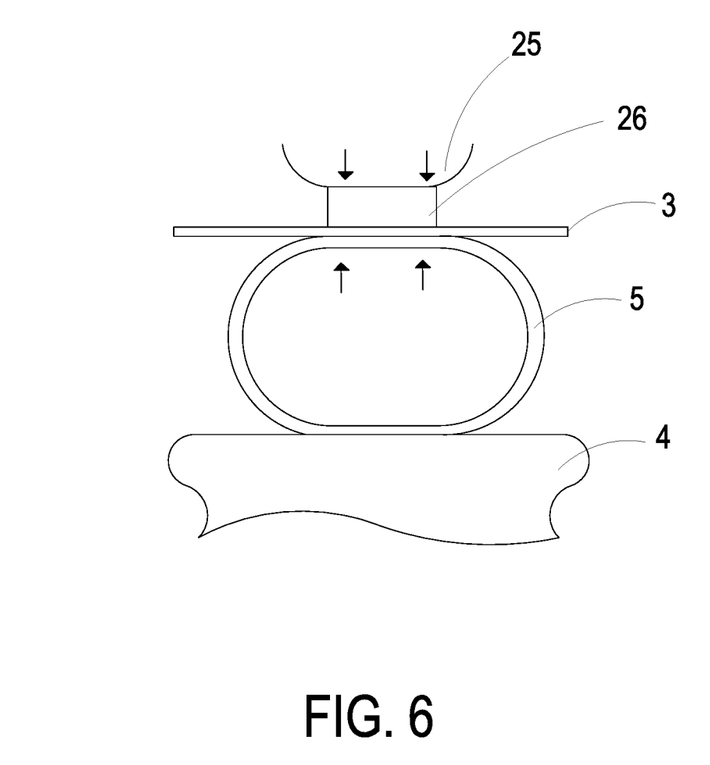
FIG. 6 schematically illustrates the scenario of using the blood pressure measuring device to measure the blood pressure value.

Please refer to FIGS. 1, 5 and 6. When the user operates the driving-and-control module 1 through the display screen 11, the gas transportation device 24 is enabled under control of the driving-and-control module 1. The ambient gas is inhaled into the elastic medium 25 by the gas transportation device 24 and collected in the elastic medium 25, so that the volume of the elastic medium 25 is expanded. As the volume of the elastic medium 25 is expanded, the pressure sensor 26 disposed on the elastic medium 25 is raised up for allowing the pressure sensor 26 to be in close contact with the user's skin 3 to measure the blood pressure value of the user. Please refer to FIG. 6. As the gas transportation device 24 is enabled to continuously push the gas to the elastic medium 25, the pressure sensor 26 is in close contact with the user's skin 3 to press against the artery 5 between the bone 4 and the skin 3. By pressing the pressure sensor 26 against the artery 5 of the user, the pressure sensor 26 measures the blood pressure value of the target artery through a scanning operation and transmits the measured blood pressure information to the driving-and-control module 1.

Figure 7:
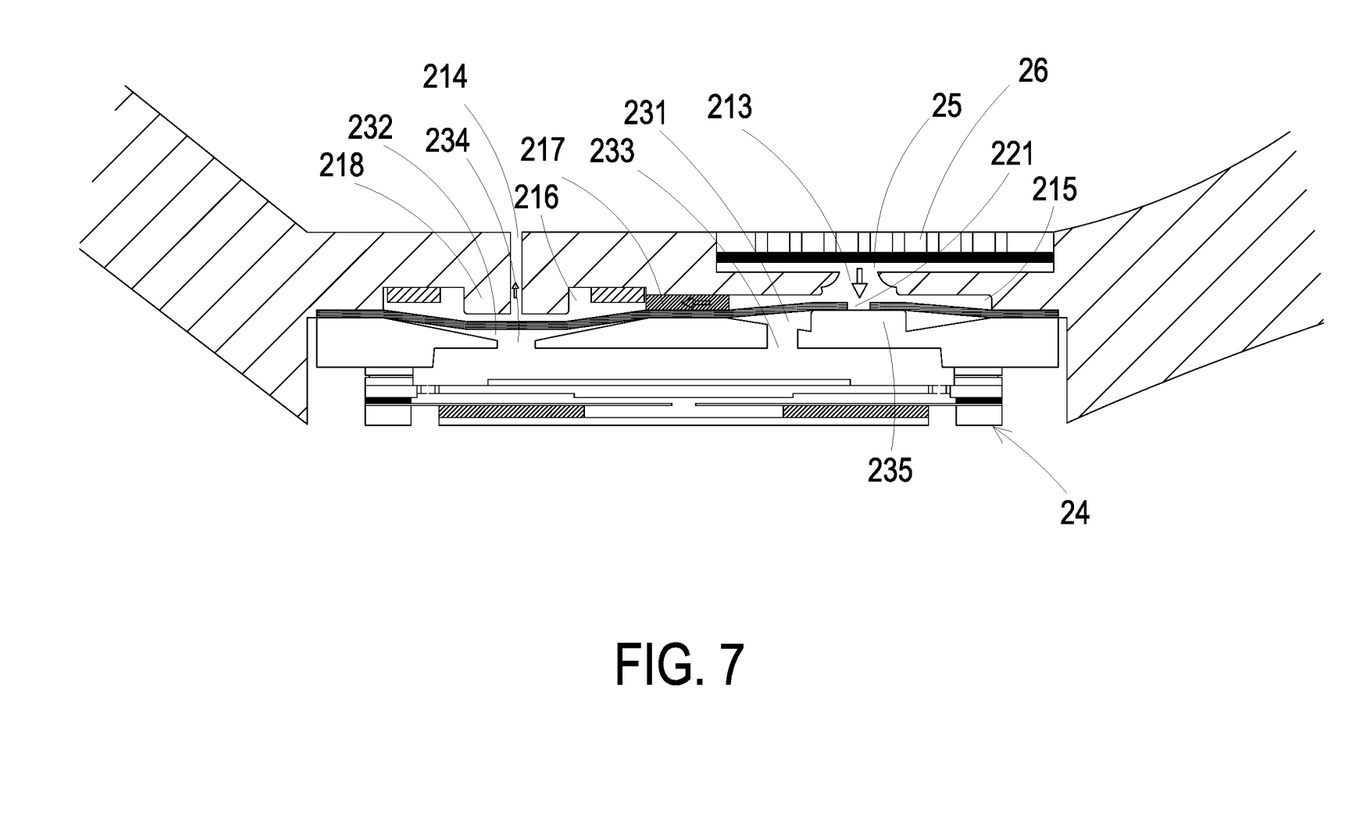
FIG. 7 is a schematic cross-sectional view illustrating the pressure-releasing action of the gas transportation device of the wearable blood pressure measuring device according to the embodiment of the present disclosure.

Please refer to FIG. 7. After the blood pressure value is measured, the gas transportation device 24 is disabled. At this stage, the inner pressure of the elastic medium 25 is higher than the pressure of any part inside the gas transportation device 24. Consequently, the gas in the elastic medium 25 is transported to the first gas-collecting chamber 215 through the gas-collecting hole 213. The gas in the first gas-collecting chamber 215 pushes the valve plate 22, so that the valve plate 22 is moved downwardly to be in contact with the gas-collecting seat 23. Under this circumstance, the valve opening 221 of the valve plate 22 is in close contact with the second convex structure 235 to close the valve opening 221 and thus the first perforation 233 is not in fluid communication with the first gas-collecting chamber 215. The second perforation 234 is also closed by the valve plate 22. Both the valve opening 221 and the second perforation 234 are closed so as to prevent the gas from returning back to the gas transportation device 24 through the first perforation 233 and the second perforation 234. At the same time, the portion of the valve plate 22 around the pressure-releasing hole 214 is separated from the first convex structure 218, and a pre-force that brings the valve plate 22 into close contact with the first convex structure 218 is eliminated. Therefore, the gas is transported from the gas-collecting chamber 215 to the first pressure-releasing chamber 216 through the communication channel 217, and then discharged through the pressure-releasing hole 214 into the environment outside the gas transportation device 24. Consequently, the pressure-releasing action is completed and the pressure sensor 26 is shrunken to the second accommodation recess 212.

From the above descriptions, the present disclosure provides the wearable blood pressure measuring device. The gas transportation device is embedded in the wristband. After the gas transportation device is enabled, the gas is transported to the elastic medium to raise the pressure sensor so that the pressure sensor is in close contact with the user to measure the blood pressure information of the user and transmit the measured blood pressure information to the driving-and-control module. The blood pressure information is transmitted to the external device through the transmission module, or the blood pressure information is directly shown on the display screen. Consequently, the blood pressure information can be measured everywhere and at any time. In addition, the wearable blood pressure measuring device has the benefits of small size, light weightiness and easy portability, and the wearable blood pressure measuring device is power-saving. In other words, the wearable blood pressure measuring device with the gas transportation device is industrially valuable.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A wearable blood pressure measuring device, comprising:
    a wristband having a mounting zone, wherein the mounting zone has a first accommodation recess, a second accommodation recess, a gas-collecting hole and a pressure-releasing hole, wherein the first accommodation recess and the second accommodation recess are in fluid communication with each other through the gas-collecting hole, and the first accommodation recess is in fluid communication with an environment outside the wristband through the pressure-releasing hole;
    a valve plate stacked on an inner surface of the first accommodation recess, and having a valve opening aligned with the gas-collecting hole;
    a gas-collecting seat disposed within the first accommodation recess and stacked on the valve plate, wherein the gas-collecting seat has plural perforations;
    a gas transportation device disposed on the gas-collecting seat, wherein the gas transportation device has a piezoelectric actuator, the piezoelectric actuator is actuated to introduce gas to the gas-collecting seat through the plural perforations, and to push the valve plate and cause the valve opening of the valve plate to be in fluid communication with the gas-collecting hole, and the gas is further guided into and collected in the second accommodation recess;
    an elastic medium covering and sealing the second accommodation recess and configured to be inflated with the gas for displacement; and
    a pressure sensor stacked on the elastic medium,
    wherein when the gas transportation device is enabled to transport the gas to the elastic medium, the elastic medium configured to inflate with the gas and expand so as to push the pressure sensor to be in contact with a measurement part of a user's body, thereby measuring a blood pressure value of a target artery through a scanning operation by pressing the pressure sensor against the measurement part.

2. The wearable blood pressure measuring device according to claim 1, wherein the pressure sensor is an array-type pressure sensor.

3. The wearable blood pressure measuring device according to claim 1, wherein the wearable blood pressure measuring device further comprises a driving-and-control module disposed on the wristband to control the gas transportation device.

4. The wearable blood pressure measuring device according to claim 3, wherein the driving-and-control module further comprises a display screen for displaying information of the blood pressure value measured by the pressure sensor.

5. The wearable blood pressure measuring device according to claim 3, further comprising a transmission module, wherein the transmission module is disposed on the driving-and-control module to transmit information of the blood pressure value of the user to an external device.

6. The wearable blood pressure measuring device according to claim 5, wherein the transmission module is a wired transmission module, wherein the wired transmission module is at least one selected from the group consisting of a USB transmission module, a mini-USB transmission module and a micro-USB transmission module.

7. The wearable blood pressure measuring device according to claim 5, wherein the transmission module is a wireless transmission module, wherein the wireless transmission module is at least one selected from the group consisting of a Wi-Fi transmission module, a Bluetooth transmission module, a radio frequency identification (RFID) transmission module and a near field communication (NFC) transmission module.

8. The wearable blood pressure measuring device according to claim 5, wherein the external device is at least one selected from the group consisting of a cloud system, a portable electronic device and a computer system.

9. The wearable blood pressure measuring device according to claim 1, wherein a first gas-collecting chamber and a first pressure-releasing chamber are concavely formed in the first accommodation recess, the first gas-collecting chamber and the first pressure-releasing chamber are in fluid communication with each other through a communication channel, the gas-collecting hole is in fluid communication with the first gas-collecting chamber, the pressure-releasing hole is in fluid communication with the first pressure-releasing chamber, a first convex structure is received within the first pressure-releasing chamber, and the first convex structure is disposed around the pressure-releasing hole.

10. The wearable blood pressure measuring device according to claim 9, wherein the gas-collecting seat further comprises a second gas-collecting chamber, a second pressure-releasing chamber and a second convex structure, wherein a first perforation of the plural perforations is in fluid communication with the second gas-collecting chamber, a second perforation of the plural perforations is in fluid communication with the second pressure-releasing chamber, and the second convex structure is disposed within the second gas-collecting chamber, wherein when the second convex structure is in contact with the valve opening of the valve plate to generate a pre-force, the valve opening is closed, wherein when the gas transportation device is enabled, the gas is introduced through the first perforation and the second perforation into the wearable blood pressure measuring device to push the valve plate, so that the valve plate is in contact with the first convex structure to close the pressure-releasing hole and the valve opening moves away from the second convex structure, wherein the gas is transported through the valve opening and then collected in the second accommodation recess through the gas-collecting hole, so that the elastic medium configured to inflate with the gas and expand to press the pressure sensor against the user's skin for measuring the blood pressure value.

11. The wearable blood pressure measuring device according to claim 9, wherein when the gas transportation device is disabled and a pressure of the collected gas in the second accommodation recess is higher than a pressure of the gas at the first perforation and the second perforation, the gas pushes the valve plate away from the first perforation to close the second perforation and open the pressure-releasing hole, and the second convex structure is in contact with the valve opening of the valve plate to restore the pre-force to close the first perforation, so that the gas is discharged through the communication channel and the pressure-releasing hole into the environment outside the wristband, wherein after the gas is discharged into the environment outside the wristband, the gas is released from the elastic medium and the pressure sensor returns to the second accommodation recess.

12. The wearable blood pressure measuring device according to claim 1, wherein the gas transportation device comprises:

a gas inlet plate having at least one inlet aperture, at least one convergence channel and a convergence chamber, wherein the at least one inlet aperture allows the gas to flow in, and the at least one convergence channel is disposed correspondingly to the at least one inlet aperture and guides the gas from the at least one inlet aperture toward the convergence chamber;

a resonance plate having a central aperture and a movable part, wherein the central aperture is aligned with the convergence chamber, and the movable part surrounds the central aperture; and     the piezoelectric actuator being aligned with the resonance plate,     wherein a gap is formed between the resonance plate and the piezoelectric actuator, so that the gas from the at least one inlet aperture of the gas inlet plate is converged to the convergence chamber along the at least one convergence channel and flows into the gap through the central aperture of the resonance plate when the piezoelectric actuator is driven, whereby the gas is further transported through a resonance between the piezoelectric actuator and the movable part of the resonance plate.

13. The wearable blood pressure measuring device according to claim 12, wherein the gas transportation device further comprises a conducting plate, a first insulation plate and a second insulation plate, wherein the gas inlet plate, the resonance plate, the piezoelectric actuator, the first insulation plate, the conducting plate and the second insulation plate are stacked sequentially.

* * * * *